(12) United States Patent
Reiterer et al.

(10) Patent No.: US 12,016,971 B2
(45) Date of Patent: Jun. 25, 2024

(54) TISSUE ENGINEERED SYNTHETIC SUPPORT STRUCTURE

(71) Applicants: Medtronic, Inc, Minneapolis, MN (US); Sofradim Production, Trevoux (FR)

(72) Inventors: Markus W. Reiterer, Plymouth, MN (US); Kimberly A Chaffin, Woodbury, MN (US); Darlene P. Nebinger, Oxford, CT (US); Angela M Throm Quinlan, Wallingford, CT (US); Michael F. Wolf, Golden Valley, MN (US); Yves Bayon, Lyon (AR)

(73) Assignees: Medtronic, Inc., Minneapolis, MN (US); Sofradim Production, Trevoux (FR)

( * ) Notice: Subject to any disclaimer, the term of this patent is extended or adjusted under 35 U.S.C. 154(b) by 275 days.

(21) Appl. No.: 17/529,816

(22) Filed: Nov. 18, 2021

(65) Prior Publication Data
US 2022/0354992 A1  Nov. 10, 2022

Related U.S. Application Data

(60) Provisional application No. 63/185,244, filed on May 6, 2021.

(51) Int. Cl.
*A61K 31/65* (2006.01)
*A61F 2/06* (2013.01)
(Continued)

(52) U.S. Cl.
CPC ............. *A61L 27/38* (2013.01); *A61F 2/06* (2013.01); *A61K 31/496* (2013.01); *A61K 31/65* (2013.01);
(Continued)

(58) Field of Classification Search
CPC ...... A61L 27/38; A61L 27/52; A61L 2400/06; A61L 2300/64; A61L 31/145;
(Continued)

(56) References Cited

U.S. PATENT DOCUMENTS

2017/0105724 A1* 4/2017 Limem ................ A61B 17/064
2019/0239875 A1* 8/2019 Prikril .............. A61B 17/06133

FOREIGN PATENT DOCUMENTS

WO    WO-2008107483 A2 * 9/2008 ............. A61L 27/34

OTHER PUBLICATIONS

Guillaume et al. (Hernia 2020;24:1233-1243). (Year: 2020).*

(Continued)

*Primary Examiner* — Ernst V Arnold
(74) *Attorney, Agent, or Firm* — Fletcher Yoder, P.C.

(57) ABSTRACT

Systems and methods for tissue engineered synthetic support structures, such as grafts and patches are provided. The systems and methods can be used to make tissue engineered planar sheathes or meshes that can be fashioned into substantially planar or non-planar 3D tissue/organ structures adaptable to structure and organs within a human or mammalian body. The systems and methods can use bioink deposited on a material having specified properties and matured under specified conditions to create the tissue engineered planar sheathes or meshes having biomechanical and biological properties tailored to a particular tissue.

18 Claims, 8 Drawing Sheets

(51) Int. Cl.

| | |
|---|---|
| *A61K 31/496* | (2006.01) |
| *A61L 27/38* | (2006.01) |
| *A61L 27/52* | (2006.01) |
| *C12N 5/077* | (2010.01) |
| *C12N 5/0775* | (2010.01) |
| *A61F 2/00* | (2006.01) |

(52) U.S. Cl.
CPC ............ *A61L 27/52* (2013.01); *C12N 5/0661* (2013.01); *C12N 5/0663* (2013.01); *A61F 2/0063* (2013.01); *A61F 2210/0014* (2013.01); *A61F 2210/0076* (2013.01); *A61F 2240/001* (2013.01); *A61L 2400/06* (2013.01); *C12N 2513/00* (2013.01); *C12N 2533/40* (2013.01)

(58) Field of Classification Search
CPC ........ A61L 31/148; A61F 2/06; A61F 2/0063; A61F 2210/0014; A61F 2210/0076; A61F 2240/001; A61F 2002/0068; A61F 2210/0004; A61F 2240/002; A61F 2250/0059; A61F 2250/0067; A61K 31/496; A61K 31/65; C12N 5/0661; C12N 5/0663; C12N 2513/00; C12N 2533/40; C12N 2533/30; C12N 5/0068; B33Y 80/00; B33Y 10/00
See application file for complete search history.

(56) References Cited

OTHER PUBLICATIONS

Zhu et al. (World of Gastrointestinal Surgery 2015;7(10):226-236) (Year: 2015).*

Atiss Fibrin Sealant [online] retrieved on Jan. 11, 2024 from: https://dailymed.nlm.nih.gov/dailymed/drugInfo.cfm?setid=92fc93e1-9695-4705-90c5-4452a80bb074; 43 pages. (Year: 2022).*

A biological hybrid model for collagen-based tissue engineered vascular constructs, Berglund et al., Biomaterials, 2003, 24, 1241-1254.

A self-renewing, tissue-engineered vascular graft for arterial reconstruction, Torikai, et al., J Thorac Cardiovasc Surg 2008;136:37-45.

Biomechanical Parameters of Mesh Reinforcement and Analysis of a Novel Device for Incisional Hernia Prevention, Messa IV, et al., Journal of Surgical Research, Feb. 2021;258:153-161.

Development of a Composite Degradable/Nondegradable Tissue-engineered Vascular Graft, Tschoeke et al., Artif Organs. Oct. 2008;32(10):800-9.

Degradable/non-degradable polymer composites for in-situ tissue engineering small diameter vascular prosthesis application, Wang et al., Bio-Medical Materials and Engineering, vol. 24, No. 6, pp. 2127-2133, 2014.

Tissue-Engineered Vascular Grafts. Reference Series in Biomedical Engineering. Springer, Cham., Fernández-Colino et al., 2020, 339-363.

Hernia repair: the search for ideal meshes, Bringman et al., Hernia. Feb. 2010;14(1):81-7.

Human Tissue Engineered Blood Vessel For Adult Arterial Revascularization, L'Heureux et al., Nat Med. Mar. 2006 ; 12(3): 361-365.

Mechanical properties of the abdominal wall and biomaterials utilized for hernia repair, Deeken, et al., J Mech Behav Biomed Mater. Oct. 2017;74:411-427.

Mechanical properties of completely autologous human tissue engineered blood vessels compared to human saphenous vein and mammary artery, Biomaterials. Mar. 2009 ; 30(8): 1542-1550.

Modified Mesh for Hernia Repair that is Adapted to the Physiology of the Abdominal Wall, Klinge, et al., Eur J Surg 1998; 164: 951-960.

Physical structure and mechanical properties of knitted hernia mesh materials: A review, Sanbhal, et al., Journal of Industrial Textiles. 19. 1266-1270.

Prosthetic Meshes for Repair of Hernia and Pelvic Organ Prolapse: Comparison of Biomechanical Properties, Maurer et al., Materials 2015, 8, 2794-2808.

Rapid fabrication of reinforced and cell-laden vascular grafts structurally inspired by human coronary arteries, Akentjew, et al., Nat Commun. Jul. 15, 2019:10(1):3098.

The Argument for Lightweight Polypropylene Mesh in Hernia Repair, Cobb, et al., Surgical Innovation, vol. 12, No. 1 Mar. 2005: pp. 63-69.

Tissue engineered vascular grafts—Preclinical aspects, Thomas et al., Int J Cardiol. Aug. 20, 2013;167(4):1091-100.

Tissue-Engineered Blood Vessels With Endothelial Nitric Oxide Synthase Activity, Lim et al., J Biomed Mater Res B Appl Biomater. May 2008;85(2):537-46.

* cited by examiner

TISSUE ENGINEERED SYNTHETIC SUPPORT STRUCTURE

CROSS REFERENCE TO RELATED APPLICATION

This application claims priority to U.S. Provisional App. No. 63/185,244, filed May 6, 2021, the entire contents of which are incorporated by reference herein.

FIELD

The disclosure relates to systems and methods for tissue engineered synthetic support structures, such as grafts and patches are provided. The systems and methods can be used to make tissue engineered planar sheathes or meshes that can be fashioned into substantially planar or non-planar 3D tissue/organ structures adaptable to structure and organs within a human or mammalian body. The systems and methods can use bioink deposited on a material having specified properties and matured under specified conditions to create the tissue engineered planar sheathes or meshes having biomechanical and biological properties tailored to a particular tissue.

BACKGROUND

Tissue engineered substantially planar sheets have broad application in neurovascular, coronary artery, peripheral arterial and venous disease, hernia repair, cardiac patches. However, the known tissue engineered materials often lack patency or fail to have sufficient mechanical properties for successful in vivo implantation. In general, three types of materials are known: autologous, synthetic, and tissue engineered. Each suffer from the known problem of insufficient or unsuitable biomechanical properties. In general, patches of tissue cannot be harvested from donors. Synthetic substantially planar sheets made from Dacron, Teflon, and other materials have been fabricated to meet the need for patches but suffer from a variety of performance issues. Known patches cannot mimic the biomechanical properties of surrounding tissue and fail after implantation due to possible failure of the mesh and/or failure of the surrounding tissue. Chronic inflammation and tissue erosion are also additional examples of tissue complications. Synthetic substantially planar sheets are susceptible to infection and lack of growth potential. Although synthetic polymers such as polytetrafluoroethylene ("PTFE"), polyester, and polyurethane have been used due to their antithrombogenic and mechanical properties, thrombus formation and infection still pose a problem.

To overcome the thrombogenic limitations of synthetic materials, tissue engineered substantially planar sheets containing autologous or allogeneic cells have been developed. However, these materials generally exhibit poor biomechanical and strength properties. Other known approaches require the use of various materials, manufacturing methods, cell sources, and culture protocols based on a scaffold using synthetic or natural materials or a decellularized natural matrix and self-assembly processes. Electro-spinning or electro-static preparation of materials have also been used to form a scaffold from various polymers. Sometimes a scaffold or stabilizing material is used to retain the autologous cell seeding during a growth period whether in a bioreactor or in vivo. Hydrogels or collagens have been used as a substrate for autologous cells such as smooth muscle cells. For the known substantially planar sheets, scaffolds are generally electro-spun or made using non-woven materials.

However, the known tissue engineered materials, whether formed via molding, electrospinning (or electro-static), seeding, or other techniques using various stabilizing constructs such as scaffolds, continue to suffer biomechanical failure. The known materials frequently result in clinical complications such as infection, chronic inflammation, or growth failure. For example, the known tissue engineered materials exhibit limitations in mechanical integrity such as insufficient suture retention. In particular, the known substantially planar sheets, patches, or meshes used in hernia treatment or cardiac patches lack sufficient tensile properties or mechanical behavior compatible to the function of surrounding native tissue. The materials often cannot withstand membrane tension typically found in the pelvic region, in the abdominal wall at rest, at high intra-abdominal pressures, or at pressures required for cardiac tissue. In addition to insufficient compliance, absorption time, and suture retention strength properties, the known tissue engineered materials cannot provide variable or different regions or areas of mechanical strength. Mismatch of mechanical properties of the implant material, as compared to surrounding native tissue can result in clinical complications. For example, hernia repair failure often occurs at the implant-tissue interface rather than from mechanical failure of the mesh material itself.

Hence, there is a need for materials, methods for manufacture, and products made therefrom that can be used to generate tissue engineered hernia meshes that exhibit adequate strength, longevity, and safety while having the desired physical properties for successful implantation in a patient. The need extends to materials, methods for manufacture, and products made therefrom for use in hernia repair and cardiac patches that can conform or are adaptable to structures and organs within a mammalian body, such as a human. The need extends to abdominal meshes. The need also includes transvaginal meshes. The need includes materials, methods for manufacture, and products made therefrom that can be bioresorbable, biodegradable, or biostable. The need extends to materials, methods for manufacture, and products made therefrom to make a tissue engineered substantially planar sheet or mesh that has sufficient mechanical properties for surgical in vivo implantation and retention. The need includes a tissue engineered material having regions of different mechanical characteristics. The need extends to materials, methods for manufacture, and products made therefrom having desirable erosion kinetics that occur after a maturation phase. The need extends to materials, methods for manufacture, and products made therefrom into a substantially planar sheet or patch that can be securely sutured in a host location. The need extends to materials, methods for manufacture, and products made therefrom that has desirable material compliance and creep properties. The need extends to materials, methods for manufacture, and products made therefrom that can withstand a specific burst pressure. The need extends to materials, methods for manufacture, and products made therefrom that has sufficient mechanical integrity. The need extends to materials, methods for manufacture, and products made therefrom that can be used in a mesh-tissue construct for an organoid. The need extends to materials, methods for manufacture, and products made therefrom having desired tensile and shear strength properties. The need extends to materials, methods for manufacture, and products made therefrom having desired erosion kinetics to match a desired absorption time. The need extends to materials, methods for manufacture, and products made therefrom having mechanical integrity. The need extends to materials, methods for manufacture, and products made therefrom that can integrate properly at an implantation site. The need extends to materials, methods for manufacture, and products made therefrom for substantially planar sheets, patches, or meshes used in hernia treatment or cardiac patches having sufficient tensile properties or mechanical behavior compatible to the function of surrounding native tissue. The need extends to materials, methods for manufacture, and products made therefrom for hernia repair or organoid patches made from regular knitted constructs. The need extends to materials, methods for manufacture, and products made therefrom having capable of withstanding membrane tension typically found in the pelvic region, in the abdominal wall at rest, at high intra-abdominal pressures, or at pressures required for cardiac tissue. The need extends to materials, methods for manufacture, and products made therefrom having variable or different regions or areas of mechanical strength. The need extends to materials, methods for manufacture, and products made therefrom that can interface and integrate with host tissue at the site of implantation and control infection. The need extends to anchoring components such as stabilization hooks that can integrate a tissue engineered construct with surrounding tissue. The need includes use of additive techniques such as 3D printing on which materials can be deposited thereon. The need extends to materials, methods for manufacture, and products made therefrom for hernia repair or organoid patches wherein the mesh or scaffold is bioinert, biodegradable, or bioabsorbable.

SUMMARY OF THE INVENTION

The problem to be solved is a tissue engineered material for medical use having suitable mechanical properties for in vivo implantation. The solution provides for a method of generating a hernia mesh having suitable biomechanical properties for medical use and surgical implantation.

The first aspect is drawn to a method. In any embodiment, the method can include the steps of forming a tissue engineered substantially planar sheet by positioning a substantially planar mesh having a plurality of stabilization anchors, onto a substrate and filling a void space in the substantially planar mesh fully or partially with a bioink to form the substantially planar sheet; and maturing the substantially planar sheet in a bioreactor.

In any embodiment, the stabilization anchor can be a hook, loop, or latch.

In any embodiment, the bioink can be placed on the substantially planar mesh by 3D printing, dip casting, or slot casting.

In any embodiment, the substantially planar mesh can be placed on a substrate and a controllable moving syringe dispensing system deposits the bioink.

In any embodiment, the substantially planar mesh can be a weave, knit, braid, non-woven textile, or laser cut metal.

In any embodiment, the substantially planar mesh can be constructed from a fast degrading polymer.

In any embodiment, the substantially planar mesh can have one or more antibiotics or antibiotic agents.

In any embodiment, the antibiotic can be minocycline and rifampin and eluted into local tissue for at least 1 day after implantation. In any embodiment, the antibiotic can also be eluted into local tissue at least any one of 2, 3, 5, 6, 7 days after implantation. In any embodiment, the antibiotic can be eluted into local tissue at least any one of 1, 2, 3, 4, 5 weeks after implantation.

In any embodiment, the substantially planar mesh can be absorbed after implantation in about 9 weeks.

In any embodiment, the substantially planar mesh can be a multi-filament knitted mesh.

In any embodiment, the substantially planar mesh can have a pore size between 0.2 and 5.0 mm, and an elasticity matching a stiffness of a target tissue or organ.

In any embodiment, the substantially planar mesh can have a pore size of at least 3 mm by 3 mm.

In any embodiment, the substantially planar mesh can have a pore size of any one of at least 2.9 mm by 2.9 mm, at least 2.5 mm by 2.5 mm, at least 2.2 mm by 2.2 mm, at least 2.0 mm by 2.0 mm, at least 1.9 mm by 1.9 mm, at least 1.5 mm by 1.5 mm, at least 1.3 mm by 1.3 mm, and at least 1.0 mm by 1.0 mm.

In any embodiment, the planar mesh can be biodegradable, bioabsorbable, or bioinert.

In any embodiment, the bioink can be seeded with endothelial cells.

In any embodiment, one or more smooth muscle cell layer, skeletal muscle cell layer, myocardiocytes, pericytes, endothelial cells, fibroblast layer, cord-blood derived cell layer, or combinations thereof can be deposited on the bioink.

In any embodiment, the bioink can include a hydrogel and cells.

In any embodiment, the hydrogel can be synthetic, hybrid or natural.

In any embodiment, the hydrogel can include substances for cross-linking by physical or chemical means.

In any embodiment, the one or more nutrition factors and signaling chemicals can be added to the growth medium in the bioreactor.

The features disclosed as being part of the first aspect can be in the first aspect, either alone or in combination, or follow any arrangement or permutation of any one or more of the described elements. Similarly, any features disclosed as being part of the first aspect can be in the second aspect, either alone or in combination, or follow any arrangement or permutation of any one or more of the described elements.

The second aspect is drawn to a tissue engineered hernia patch produced by the method described in the first aspect wherein the hernia patch can have a burst strength of at least 250 kPa, tensile strength of at least 100 N, and suture pull out strength of at least 25 N.

In any embodiment, the tissue engineered hernia patch can also contain or be surrounded by an anti-bacterial envelope.

In any embodiment, the anti-bacterial envelope can contain the antimicrobial agents minocycline and rifampin.

The features disclosed as being part of the second aspect can be in the second aspect, either alone or in combination, or follow any arrangement or permutation of any one or more of the described elements. Similarly, any features disclosed as being part of the second aspect can be in the first aspect, either alone or in combination, or follow any arrangement or permutation of any one or more of the described elements.

DETAILED DESCRIPTION

Figure 1:
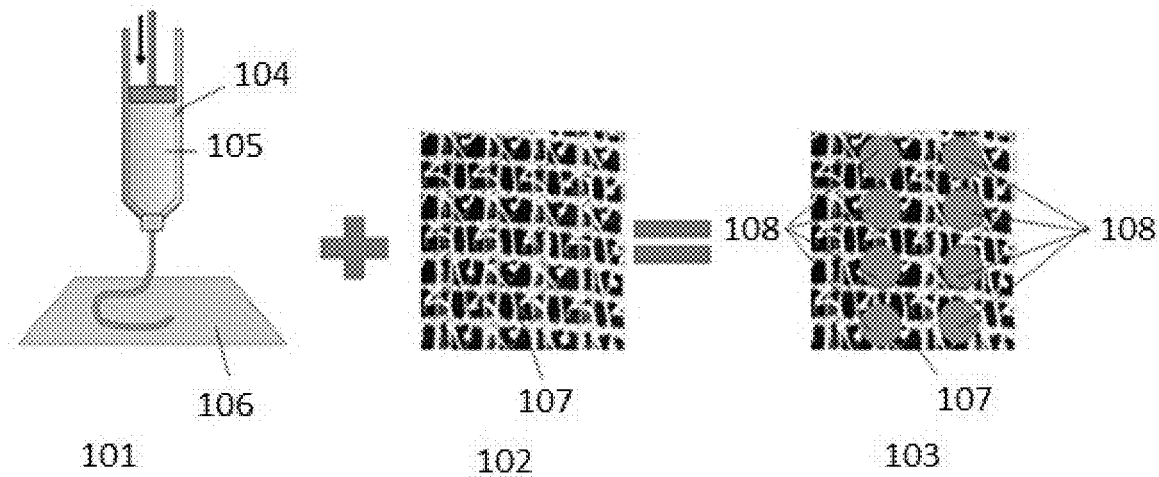
FIG. 1 illustrates a process of depositing bioink on a mesh with Velcro-like hooks.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "absorbed" refers to a process of absorbing or assimilating substances into cells or across the tissues and organs via diffusion or osmosis.

The term "antibiotic," "antibiotics," "antibiotic agents," and the like refer to any substance, chemical, or compound of any aspect, portion, or percent content, that is an antimicrobial substance active against bacteria.

The term "braiding" or "braid" refers to a process or resulting construct made by interlacing any number of threads or filaments in such a way that the threads or filaments cross one another. Braiding or braided is defined under the broadest definition to be any means, method, or procedure known to those of skill in the art to form a regular geometry of the filaments by braiding, weaving, knitting, or similar process. The braided filaments can be made of threads, cords, lines, string, or any other filaments that are interlaced, knitted, woven, or weaved together in any form or configuration using any known suitable material for the intended use.

The term "bioabsorbable" refers to a material that can be degraded and adsorbed into tissue.

The term "biodegradable" refers to a material that can be transformed or altered by an organism.

The term "bioinert" refers to a material that does not interact chemically with surrounding tissues of an organism.

The term "bioink" can be any substance containing one or more type of cells, e.g., autologous cells, of any kind and a carrier material of any type. Typically, the "bioink" will be formulated for deposition using an additive technique such as 3D printing or similar, however, such requirement is not always necessary. The broadest scope of "bioink" is intended without any limitation, or actual use in a 3D printing technique.

A "bioreactor" is a structure in which a biological process is carried out.

The term "cells" refers to the basic membrane bound unit of an organism.

A "cell layer" is a layer of any thickness comprising one or more cells, as described herein.

"Cell growth medium" refers to a composition containing water, nutrients, and cell signaling chemicals necessary to cause immature cells to mature and proliferate.

"Cell signaling chemicals," or cytokines, are molecules that cause cells to control a process.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

A "controllable moving syringe" is a receptacle with a nozzle through which fluid can exit the receptacle connected to or part of a system that can be programmed to move in a specified manner.

The term "cord-blood derived cell" refers to cells either taken from or derived from cells taken from the umbilical cord and/or placenta.

A "cord-blood derived cell layer" is a layer of any thickness comprising one or more fibroblast cells, as described herein.

The phrase "cross-linking" with respect to "hydrogels" as defined herein, refers to any process whereby the mechanical integrity and degradation resistance of a hydrogel can be changed by chemical, biochemical, or physical means. For example, the hydrogels can respond to physical inputs such as temperature, pressure, and light. The hydrogels can also respond to chemical inputs such as pH, glucose, oxidants, and biological agents such as enzymes or amino acids.

The term "delivers" refers to eluting, depositing, or releasing a component, such as a drug, from a component or material.

The term "deposit" or "depositing" refers to the process of placing a material onto or within a second material by any means, method, or process. "Depositing" can encompass a variety of methods of placing the material onto or within the second material, including but not limited to, 3D printing, dip casting, or slot casting.

The term "dip casting" refers to any process whereby one component is dipped into a liquified material and then solidified by any means. For example, a male permanent mold can be dipped into a liquified material and then removed from liquified material to solidify on the male mold before the solidified shell is removed.

The term "elasticity" refers to a material's property to regain a first shape after being deformed by one or more forces at one or more points along a perimeter of the material.

"Endothelial cells" are cells that line human blood vessels.

The term "endothelial cell layer" refers to a layer of cells of a type found lining the interior of blood vessels, lymph vessels, and the heart.

A "fast-degrading polymer" is a polymeric material that will degrade under expected conditions in shorter time relative to another time. In one non-limiting embodiment, a "fast-degrading" polymer implanted in an organism can degrade within 3 months. In one non-limiting embodiment, a "fast-degrading" polymer implanted in an organism can degrade within 2 months. In one non-limiting embodiment, a "fast-degrading" polymer implanted in an organism can degrade within 1 month. A person of ordinary skill will understand the relative quickness described as being "fast-degrading" will depend on the material, application, and location in which the material degrades. Notably, one application of a fast-degrading material can be during manufacturing. For example, during maturation in a bioreactor, a fast-degrading polymer can degrade in a range of 3 to 14 days. In vivo, a fast-degrading material can degrade in a range of 1 to 3 months. One of ordinary skill will understand that fast degrading can depend and be selected to the desired application, as described herein.

A "fibroblast" or "fibroblast cell" is a biological cell that synthesizes an extracellular matrix and collagen by producing a structural framework (stroma) for tissues.

A "fibroblast layer" is a layer of any thickness comprising one or more fibroblast cells, as described herein.

The term "forming," or to "form" refers to combining together parts or components to generate a material or object of any type.

"Growth medium" refers to a composition containing water, nutrients, and cell signaling chemicals necessary to cause immature cells to mature and proliferate.

The term "hernia patch" or "hernia substantially planar sheet" and the like refer to a medical support structure used to repair or cover a hole or weak spot on a tissue or organ. For example, the hernia patch can be used to cover or patch a hole on an organ, intestine, fatty tissue, muscle, or connective tissue.

The term "hybrid" hydrogel refers to a hydrogel, as defined herein, containing a network of both synthetic and natural polymers in any combination.

The term "hydrogel" refers to a hydrogel is a three-dimensional (3D) network of hydrophilic polymers that can swell in water and hold water while maintaining the structure due to chemical or physical cross-linking of individual polymer chains. One or more components of any suitable type can be added to the hydrogel.

A "hook" refers to any curved or angular piece that can be used to catch and hold fast a material or component.

The term "knitting" refers to a process of interlacing thread or filaments in a series of connected loops. The term "knitted" describes a component fabricated by the process of "knitting."

The term "laser cut metal" refers to a metallic substance shaped by cutting the metal with a laser beam.

A "latch" refers to any component or piece or portion of a material sliding or fitting into a catch, groove, or hole to hold fast a material or component.

The phrase "local tissue" refers to tissue generally adjacent to a point to which the locality is being measured. The specific diameter or size range of the local tissue will depend on vasculature, morphology, and other factors known to one of skill in the art.

A "loop" refers to a portion of a cord or line that is folded or doubled upon itself leaving an opening between the folder portions. As used herein, the loop can be used to catch and hold fast a material or component.

The terms "maturing" or to "mature" when referring to cells refers to the process of undergoing developmental changes for a cell to attain another functional state.

The term "mesh" refers to any knit, woven, or knotted fabric of any type. In general, the mesh can be comprised of porous material made of a network of wire or thread of any type.

The term "minocycline" refers to a tetracycline antibiotic.

The term "multi-filament" means having two or more filaments of the same or different type.

The term "cardiomyocyte" refers to a heart muscle cell.

The term "natural" hydrogel refers to a hydrogel, as defined herein, containing a network of naturally derived polymers.

"Non-woven textiles" are fabrics created by methods other than weaving, knitting, or braiding. For example, nonwoven textile can be made from polymers such as PTFE or staple fibers and long fibers bonded together by chemical, mechanical, heat or solvent treatment.

The term "nutrients" or "nutrient factors" refer to any chemicals or biochemicals used by living cells.

The term "pericyte" refers to a multi-functional mural cell in the microcirculation that can wrap around endothelial cells that surround the vasculature of the body.

The terms "placing" or to "place" refer to positioning a material or component in a specified location relative to other materials or components.

The term "substantially planar mesh" refers to any mesh formed into a plane having the same general thickness. The plane is substantially larger in two dimensions than in the third dimension, and can be flat or have a curvature in 1 or 2 dimensions. In certain embodiments, a substantially planar mesh can be designed to ultimately take on the shape of non planar geometries, such as tubes with an overlapping or non-overlapping seam to form synthetic tubular organs such as blood vessels.

The term "substantially planar sheet" or "substantially planar sheet" refers to any material formed into a plane having the same general thickness. The plane is substantially larger in two dimensions than in the third dimension, and can be flat or have a curvature in 1 or 2 dimensions.

The term "pore size" refers to a distance between two opposite walls of a pore. For example, a cylindrical pore can have a pore size being the diameter of the cylindrical pores. The pore size can be a nominal or estimated value that can depend upon the method employed to determine a porosity. The pore can be any shape from ranging from an irregular shape to a symmetrical such as a circle, oval, square opening, and the like.

The terms "position," "positioned," "positioning," and the like, refer to placing a material or component in a specified location relative to other materials or components.

The term "rifampicin" refers to a polyketide belonging to a chemical class of compounds termed ansamycins that is used as an antibiotic.

The terms "seeding" or to "seed" refer to a process of placing cells to be grown onto a material.

"Signaling chemicals," or cytokines, are molecules that cause cells to control a process.

The term "slot casting" refers to process of depositing a thin liquid film onto a substrate. The film thickness of the liquid film can be controlled by the flow rate and speed of the deposition means.

The term "smooth muscle cells" refers to any non-striated muscle cells generally found lining the inside of hollow organs.

The term "smooth muscle cell layer" refers to a layer of non-striated muscle cells.

The term "synthetic" hydrogel refers to a hydrogel, as defined herein, containing a network of synthetic polymers. Any combination of one or more synthetic polymers is contemplated.

A "stabilization anchor" refers to any device to hold fast or resist movement of a component or material.

The term "stiffness" as used herein, refers to a measurement of an object's ability to resist deformation to an applied force.

The term "substrate" refers to any base material upon which another one or more material can be deposited thereon.

The phrase "suture pull out strength" refers to a mechanical or material strength of a tissue-engineered material relative to surrounding tissue and representing the force to hold a suture with or without the suture tearing.

The phrase "target organ" refers to an organ that is to be affected by an action or development. For example, a substantially planar mesh can have features that match the small intestine, which is the "target organ," of the substantially planar mesh.

The phrase "target tissue" refers to a tissue that is to be affected by an action or development. For example, a substantially planar mesh can have features that match an abdominal wall, which is the "target tissue," of the substantially planar mesh.

The term "tensile strength" refers to the highest stress a material can withstand without breaking when the material is pulled or stretched in any direction.

The term "three-dimensional printing" or "3D printing" is a type of additive manufacturing using a CAD model or a digital 3D model. The process can include material being deposited, joined, or solidified under computer control to create a three-dimensional object.

The phrase "tissue-engineered" with respect to a substantially planar sheet, patch or any other structure described herein, refers to any biomaterial, natural material, or combinations thereof, combined or formed into any type of tissue.

The term "void space" generally correlates to a porosity of the material. The term refers to empty space in material.

The term "weaving" or a "weave" refers to a process of interlacing threads or filaments to create a fabric.

The term "woven" can refer to any material or component fabricated by interlacement of warp and weft yarn. In general, warp and weft are the two basic components used in weaving wherein lengthwise or longitudinal warp yarns are held stationary in tension on a frame or loom while the transverse weft is drawn through and inserted over-and-under the warp.

Tissue Engineered Planar Mesh

FIG. 1 shows a process for fabricating a substantially planar sheet that can be used in hernia and organ repair. A deposition syringe 104 can extrude bioink 105 containing any suitable material including suitable cells, such as autologous cells suspended in a carrier material onto sheet 106, as illustrated in image 101. The sheet 106 can have Velcro-like hooks 107 to provide anchoring, as shown in the closeup image 102. Alternative stabilization anchors such as a hook, loop, latch, pins, and the like can be used as known to those of skill in the art. Bioink drops 108 delivered in the bioink 105 can then integrate into the sheet 106 by interfacing with the hooks 107, as illustrated in image 103. The sheet 106 can also have a mesh with absorbable hooks on the mesh to secure to surrounding tissues, e.g. ProGrip™ mesh. The hooks can be constructed from any suitable material such as sutures to The provided structure can encourage cell growth throughout a three-dimensional mesh space. The provided structure can encourage cell growth throughout a three-dimensional mesh space.

The substantially planar mesh or patches can utilize a mesh scaffold based on poly(lactide acid) (PLA) chemistry. In any embodiment, the geometry and mechanical properties of the scaffold can be tailored to create a scaffold capable of bearing a mechanical load in a mechanically dynamic environment. The substantially planar mesh or patches can be fabricated into tissue engineered support structures using the described methods for manufacture, and constructs made therefrom. The substantially planar mesh or patches can be used for tissue engineered hernia repair sheets, pelvic and transvaginal meshes, cardiac patches, and compositions having regions of varying biomechanical properties. The substantially planar mesh or patches can use a bioink deposited or impregnated into a scaffold made from a mesh, knitted or woven material, suture materials, inter alia, to form a hybrid structure such as a scaffold having suitable biomechanical properties for patches for surgical repair of tissues.

In any embodiment, the scaffold can provide an anchor for sutures that can secure the engineered tissue construct into surrounding tissue. Notably, an open structure provided by the void areas can allow for an interpenetrating tissue geometry, where growing tissue can encapsulate a strut of the scaffold in any of the described meshes or fabrics. The void areas or pores of the support structure can be of any geometry or shape. For examples, the void areas can be rectangular, circular, or triangular. The void areas or pores of the support structure can have a size generally in the range of at least 1 mm×1 mm. In other embodiments, the void areas or pores can be greater than 1.5 mm×1.5 mm.

In any embodiment, a deposited material can rely on an inherent strength provided by the scaffold, rather than depending on an interfacial adhesion between the scaffold and maturing tissue surrounding the implanted construct, to maintain fixation after implantation. In any embodiment, a mesh design can improve nutrient transfer into the engineered construct and host tissue integration. One of ordinary skill can determine a suitable cell density for a particular tissue type, nutrient, and oxygen supply. The mesh design can improve vascularization of the construct after implantation. One of ordinary skill can select materials and techniques such that the scaffold degrades after tissue maturation and implantation.

The supporting structures such as a fabric, braid, mesh, scaffold and the like, can degrade after any one of the following: the tissue construct has reached maturity in a bioreactor, undergone an implantation procedure, or achieved adequate host tissue integration. The supporting structures can also degrade sequentially. For example, one portion can degrade after having reached maturity in a bioreactor, a second portion degraded after implantation, and a third portion after host tissue integration.

In any embodiment, the rate of tissue growth and printed cell maturation can be faster than the rate at which any of the described scaffolds, meshes, meshes, and constructs degrade. In any embodiment, the tissue engineered hernia patch or mesh can have a resistance to mechanical fatigue of at least 20 weeks to cover a wound repair/regeneration process. In any embodiment, the tissue engineered hernia patch or mesh can degrade to substantial disappearance. The tissue engineered hernia patch or mesh can degrade after about 20 weeks. In certain embodiments, the tissue engineered hernia patch or mesh can degrade before 3 years. In other embodiments, the tissue engineered hernia patch or mesh can degrade before 2 years. In other embodiments, the tissue engineered hernia patch or mesh can degrade before 1 year. To repair a defect, the tissue engineered hernia patch or mesh can degrade at least around the same time as required for a wound repair, regeneration, or healing process. The tissue engineered hernia patch or mesh can be engaged to surrounding tissue and have biomechanical properties about the same as surrounding tissue, such as an abdominal wall area, prior to degrading any degradable portions.

In any embodiment, the tissue engineered hernia patch or mesh can have sufficient mechanical strength for a desired application. The tissue engineered hernia patch or mesh can sufficiently resist any one or more uniaxial tension, biaxial tension, and cyclic loading. In any embodiment, the tissue engineered hernia patch or mesh can have a burst strength of at least 250 kPa as described herein. In any embodiment, the tissue engineered hernia patch or mesh can have a tensile strength of at least 100 N. In any embodiment, the tissue engineered hernia patch or mesh can have suture pull out strength of at least 25 N. In any embodiment, the tissue engineered hernia patch or mesh can withstand an alternating stress force from about 0.01 N/cm to about 20 N/cm. In any embodiment, the tissue engineered hernia patch or mesh can withstand cyclic loading as might be required during a maturation phase in a bioreactor. In any embodiment, the tissue engineered hernia patch or mesh can withstand an abdominal wall pressure of between 0.2 kPa and 35 kPa. In any embodiment, the tissue engineered hernia patch or mesh can withstand an alternating tensile stress in a range of about 0.2 kPa and 35 kPa.

In any embodiment, the tissue engineered hernia patch or mesh can have material properties sufficient to support a loading on an abdominal wall. The tissue engineered hernia patch or mesh can have an elasticity matched to an abdominal wall having a Young's modulus of 42.5±9.0 kPa and/or 22.5±2.6 kPa depending on a direction (Song, Chengli, et al. "Mechanical properties of the human abdominal wall measured in vivo during insufflation for laparoscopic surgery." *Surgical Endoscopy And Other Interventional Techniques* 20.6 (2006): 987-990). In other embodiments, an elasticity matched to an abdominal wall can range from 5 to 50 MPa as an elastic matching stiffness depending on the particular properties of the abdominal wall. In other embodiment, an elasticity matching a membrane stiffness of a target tissue or organ can be between around 0.675 and around 1.26 N/mm (Maurer, Manfred M., et al. "Prosthetic meshes for repair of hernia and pelvic organ prolapse: Comparison of biomechanical properties." *Materials* 8.5 (2015): 2794-2808).

In any embodiment, the tissue engineered hernia patch or mesh can have material properties sufficient to support a surgical connection to surrounding native tissue. In any embodiment, the tissue engineered hernia patch or mesh can be sized to repair a small or medium ventral hernia. In any embodiment, the tissue engineered hernia patch or mesh can be roughly in the shape of a circle and have a diameter less than 4 cm. In any embodiment, the tissue engineered hernia patch or mesh can be roughly in the shape of a square or rectangle and have a suitable perimeter matched to an area designated for repair. In any embodiment, the tissue engineered hernia patch or mesh can be sized to repair a small incisional hernia. In any embodiment, a generally rectangular tissue engineered hernia patch or mesh can be sized to have a width less than 4 cm. In any embodiment, the tissue engineered hernia patch or mesh can be sized to repair a large ventral hernia. In any embodiment, the tissue engineered hernia patch or mesh can be roughly in the shape of a circle and have a diameter of 4 cm in diameter. In any embodiment, a rectangular tissue engineered hernia patch or mesh can be sized to repair a medium incisional hernia. In any embodiment, a rectangular tissue engineered hernia patch or mesh can have a width between 4 and 10 cm. In any embodiment, a rectangular tissue engineered hernia patch or mesh can be sized to repair a large incisional hernia. In any embodiment, the tissue engineered hernia patch or mesh can be roughly in the shape of a circle and have a diameter equal to or greater than 10 cm in diameter. In any embodiment, a rectangular tissue engineered hernia patch or mesh can have a width equal to or greater than 10 cm.

In certain embodiments, the tissue engineered hernia patch or mesh can be treated with an anti-bacterial. In other embodiments, the tissue engineered hernia patch or mesh can be encased in an anti-bacterial envelope. In any embodiment, the anti-bacterial envelope is bioabsorbable. In one non-limiting embodiment, the anti-bacterial envelope is the TYRX Absorbable Antibacterial Envelope. The anti-bacterial envelope can also contain the antimicrobial agents minocycline and rifampin.

In any embodiment, the tissue engineered hernia patch or mesh, can have areas of different stiffness based on a desired application. For example, a surgical mesh for hernia repair can have first stiffness in one region of the mesh, and a second stiffness in second region of the mesh. Notably, the surgical mesh can have one, two, three, or more regions of different stiffness.

The substantially planar mesh can be made of any nonwoven textile, yarn, suture material, woven textile, knitted textile, or braided textile of any design or suitable material. In other non-limiting embodiments, the substantially planar mesh can be made from any one or combination of a biodegradable, bioabsorbable, or bioinert material, as described herein.

The system can be an additive 3D printer or similar machine, as described herein, or otherwise known to those of ordinary skill. The substantially planar mesh can be single filament or multi-filament and constructed from fabric or any other suitable material, as already described and further provided herein. As illustrated in FIG. 1, a bioink 105 can be deposited on top of the mesh 106. Alternatively, the bioink can be printed using a bioprinter, 3D printing, or other additive technique onto the mesh, as described herein. The bioink can be seeded with additional suitable cells such as autologous cells, as described herein. In one embodiment, a controllable moving deposition process such as an automated syringe can evenly distribute and deposit the bioink on the mesh. Once the bioink has been deposited, the construct can be placed into a bioreactor and matured.

Bioink

In any embodiment, the bioink can include any suitable cells including, but not limited to autologous cells, used to create the tissue engineered support structure by a carrier material such as a hydrogel. The autologous cells can be bone marrow derived mesenchymal stem cells (MSCs), vascular smooth muscle cell (SMCs)-like cells, and endothelial cell (ECs)-like cells. One of skill can derive other possible cells having anti-thrombogenic properties or features that can aid cell implantation and successful host integration.

In any embodiment, the hydrogels can define a desired volume and provide structural integrity for a required time. The hydrogel can be a three-dimensional (3D) network of hydrophilic polymers that can swell in water and hold a large amount of water while maintaining the structure due to chemical or physical cross-linking of individual polymer chains. In any embodiment, the hydrogels can be used as agents for filling vacant spaces, carriers for delivery of bioactive molecules, and 3D structures that act as a support for cells to assist in the formation of tissue. In any embodiment, the hydrogel can be a hydrophilic polymeric network that is cross-linked to produce an elastic structure. Any technique which can be used to create a cross-linked polymer can be used to produce a hydrogel as desried herein. Copolymerization/cross-linking free-radical polymerizations can be used to produce hydrogels by reacting hydrophilic monomers with multifunctional cross-linkers. Water-soluble linear polymers of both natural and synthetic origin can be cross-linked to form hydrogels as known to those of skill in the art. Any of the various polymerization techniques can be used to form gels, including bulk, solution, and suspension polymerization.

Figure 2A:
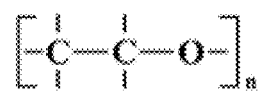
FIGS. 2A-C show embodiments of synthetic hydrogels.
Figure 2B:
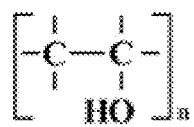
Figure 2C:
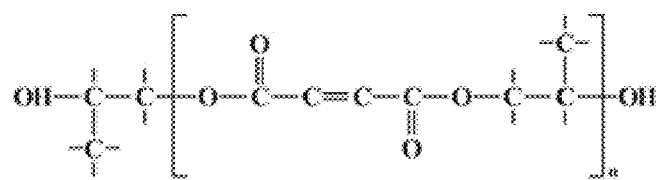

In certain embodiments, the bioink can be formed from a natural hydrogel, a synthetic hydrogel, or a hybrid of both synthetic and natural hydrogel. Both synthetic and naturally derived materials can be used to form the hydrogels for tissue engineering scaffolds in the bioink layer. FIG. 2A-C show examples of polymeric synthetic materials which can be used to form hydrogels. Poly(ethylene oxide) (PEO) as shown in FIG. 2A, poly(vinyl alcohol) (PVA) as shown in FIG. 2B, and poly(propylene fumarate) (PPF) as shown in FIG. 2C are representative synthetic polymers. In any embodiment, the synthetic hydrogels can be designed to have a specified structure and properties.

Figure 3A:
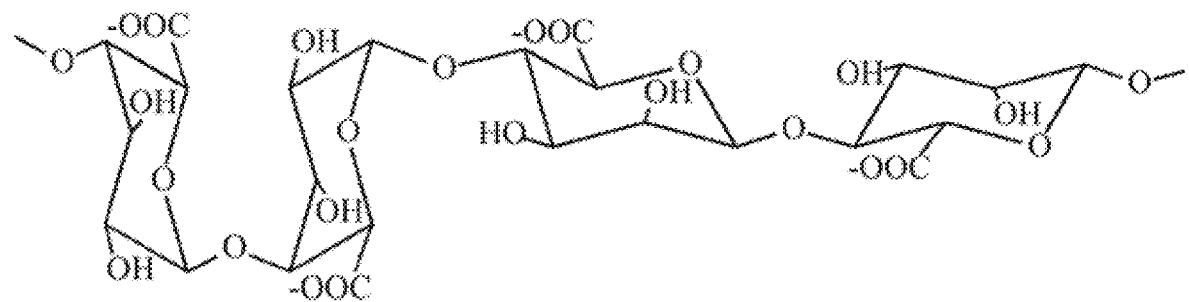
FIGS. 3A and 3B show embodiments of naturally-derived hydrogel-forming polymers.
Figure 3B:
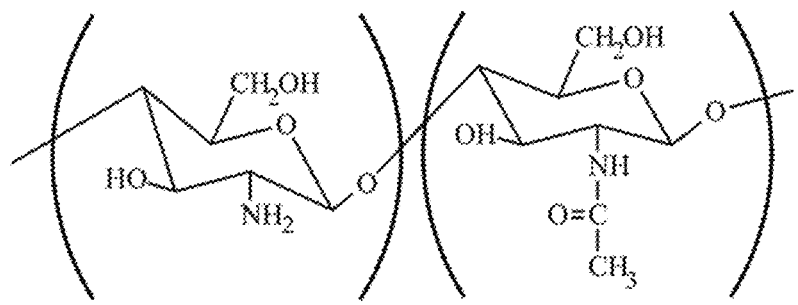

Naturally-derived hydrogel-forming polymers can also be used as tissue engineering scaffolds. For example, extra cellular matrix derived hydrogels can be used. Gelatin methacryloyl (GelMA), fibrin, or a combination of both can be used as the hydrogel. Depending on the printing or additive system used to deposit the bioink, hydrogels that are light curable can be used. The bioink can also mechanically interlock with the mesh to ensure integrity. In any embodiment, hydrogel scaffolds based on alginate as shown in FIG. 3A, chitosan as shown in FIG. 3B, and collagen can be used. In any embodiment, a homopolymer such as of poly(2-hydroxyethyl methacrylate) (PHEMA), 2-Hydroxyethyl methacrylate (HEMA), or polyethylene glycol (PEG) can be used. A cross linker such as polyethylene glycol dimethacrylate or TEGDMA (triethylene glycol dimethacrylate). One of ordinary skill can combine different hydrogels suitable for cellular proliferation and function.

Figure 4A:
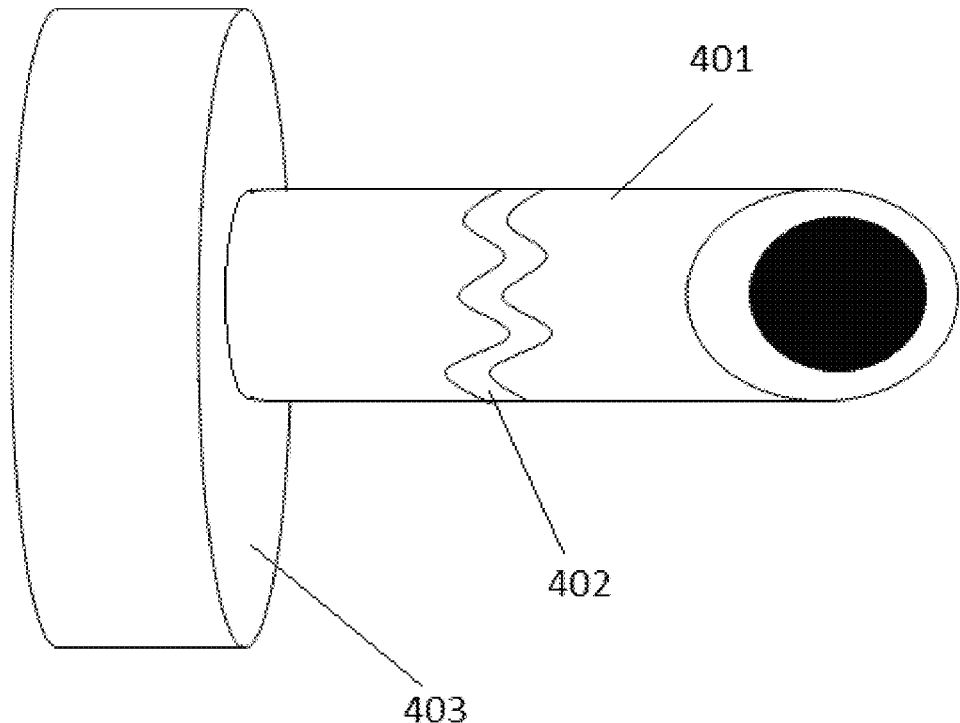
FIGS. 4A-E show a process of creating a substantially planar sheet using laser cut metal.
Figure 4B:
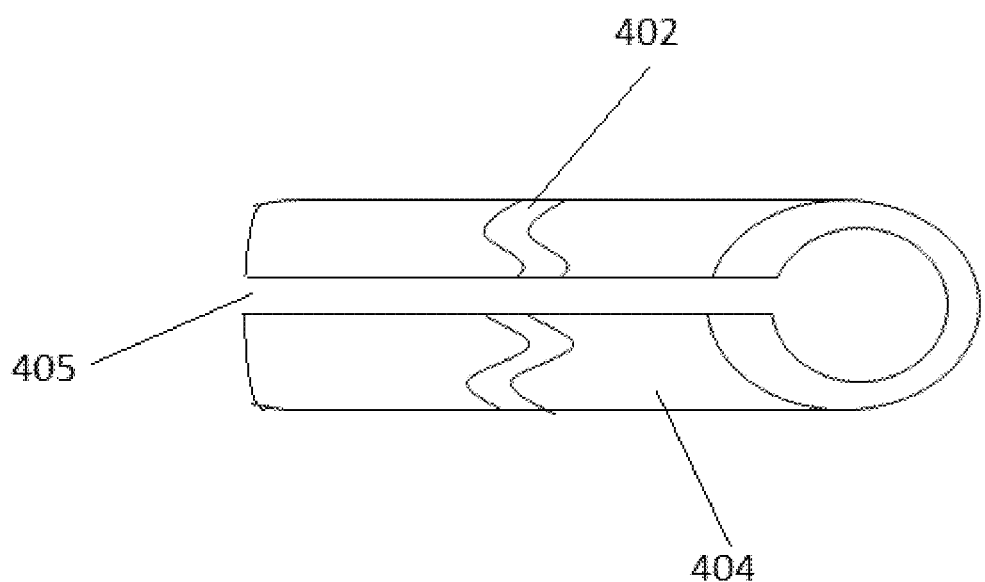

In addition to woven or non-woven textiles, the substantially planar mesh can be made from a laser cut metal, such as a nitinol tube or sheet. FIGS. 4A-E show a process of making a substantially planar mesh from a nitinol tube. For medical device purposes, nitinol is generally made in a tube form, such as nitinol tube 401 illustrated in FIG. 4A. Slots 402 are cut into the nitinol tube 401 to enable stretching. The nitinol tube 401 can be placed in a chuck 403, or other device to hold the nitinol tube 401. A laser (not shown) can be used to cut the tube open to result in cut nitinol tube 404 as illustrated in FIG. 4B. The laser cut 405 results in a cut tube 404, with the slots 402 remaining.

Figure 4C:
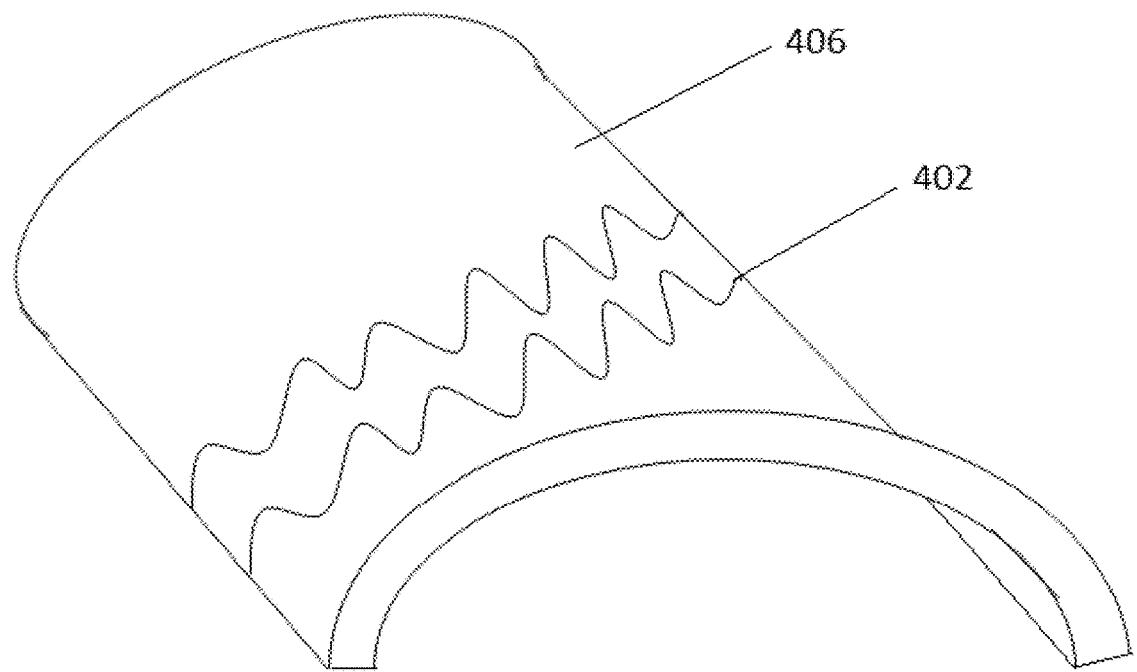
Figure 4D:
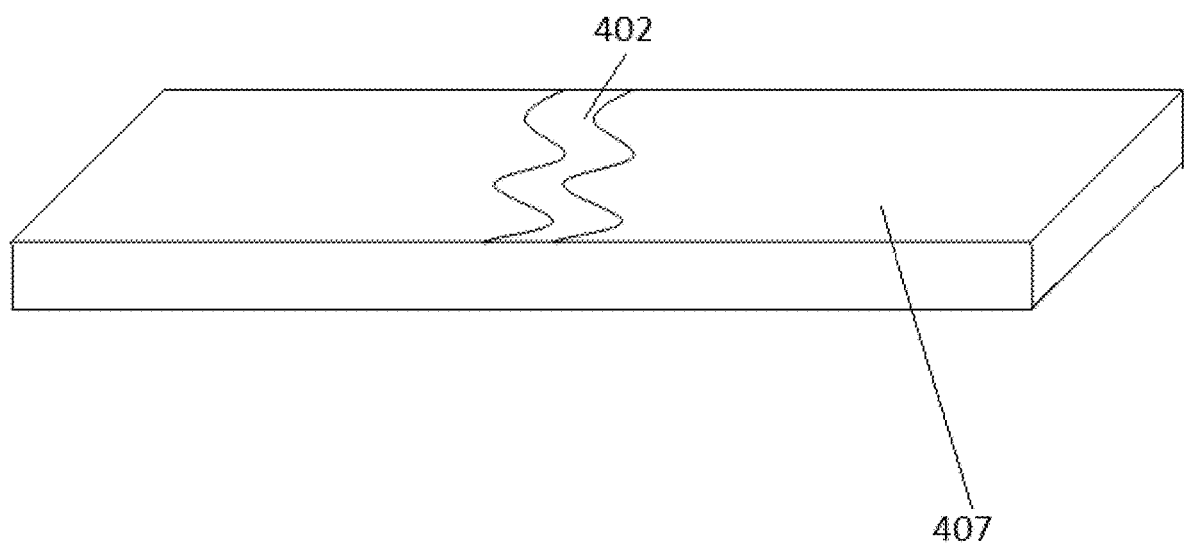
Figure 4E:
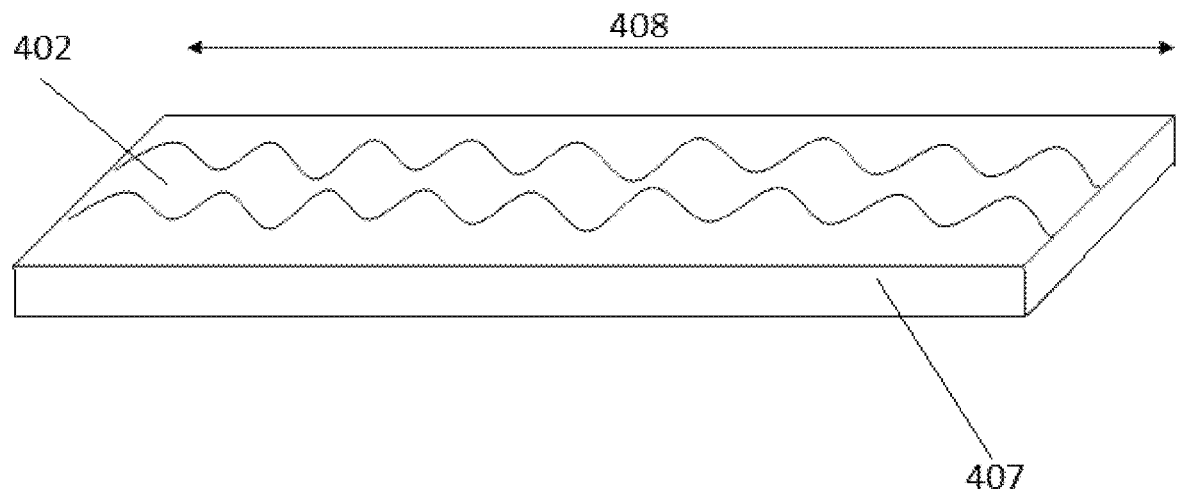

Opening the cut tube along the cut line gives open tube 406, as illustrated in FIG. 4C. The open tube 406 can be opened all of the way to give flat nitinol sheet 407 as shown in FIG. 4D. As illustrated in FIG. 4E, the flat nitinol sheet 407 can be expanded along the slots 402 in the direction of arrows 408. As an alternative, the process can start with a flat metal sheet, such as flat nitinol sheet 407 illustrated in FIG. 4D. The sheet can be expanded as shown in FIG. 4E without the need to start from a tube.

Dip Casting and Slot Coating

Figure 5:
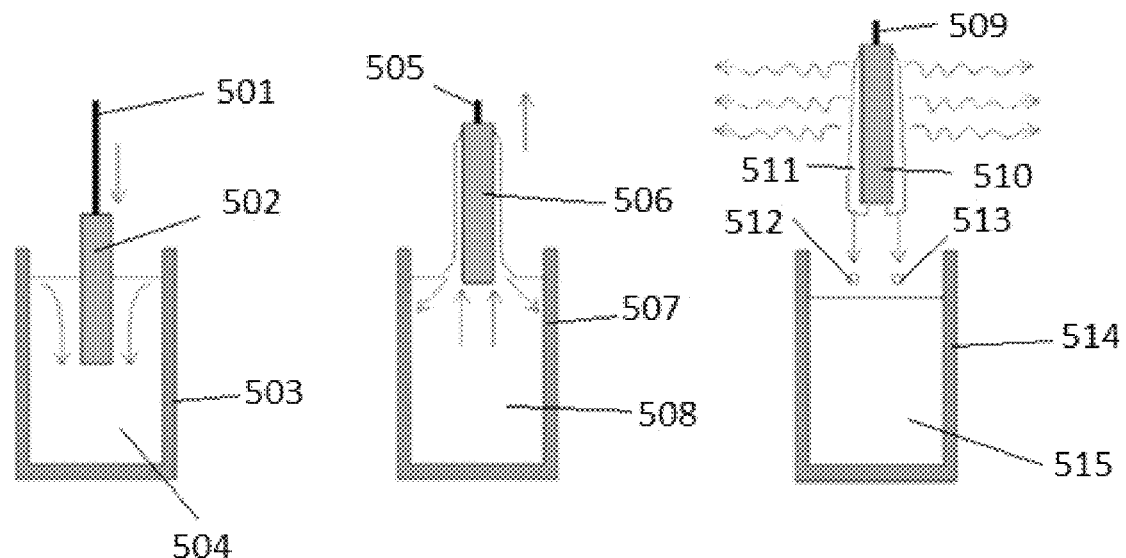
FIG. 5 illustrates a process of dip-coating.

FIG. 5 shows a dip casting process. In any embodiment, any of the materials used for the synthetic support structures can be fabricated using the described dip casting process. For example, a mechanism 501 or such as a rod can be reversibly connected to a component 502 that forms the cast or deposition surface for a synthetic support structure. The component 502 can be a plate or a substantially planar surface on which a material can be deposited or coated thereupon. The mechanism 501 can move vertically up and down to dip the component 502 into a vat 503 containing a solution 504. The mechanism 501 can be controlled to move at a constant or variable speed or in any suitable direction or motion as required. The component 502 can be immersed into solution 504 and then raised wherein the component 502 is now covered in a material layer 506. For example, the solution 504 can contain a bioink solution. The mechanism 501 can be lowered to immerse the component 502 into solution 504. The component 502 can be dipped as many times as desired into solution 504 to additively build layers onto mechanism 501. The drying process of the component 502 can be performed by leaving the component 502 in a vertical position. The dip casting process can be adjusted based on the desired curing time and material properties of the solution 504. The viscosity and temperature of the material, manufacturing environment, and curing time can be adjusted as desired. The mechanism 501 can also retain an uncoated section 505 and be pulled upwards out of vat 507 and solution 508 for drying, curing, or maturation. In a position 509, the component 510 covered by material layer 511 can evaporate to form a coating. Droplet 512 and droplet 513 can fall back into solution 515 in vat 514 to conserve material. A controller can be used to set an upper and a lower position of the component 510, immersion/withdrawal speed of the mechanism 501, and a submersion period in solution 504, solution 508, or solution 515. Any suitable material can be contained in the described solutions.

One of skill in the art will understand that the resulting substantially planar sheet is a sheet that is substantially larger in two dimensions than in the third dimension. The substantially planar sheet can be flat or can have a curvature in one or two dimensions.

Figure 6A:
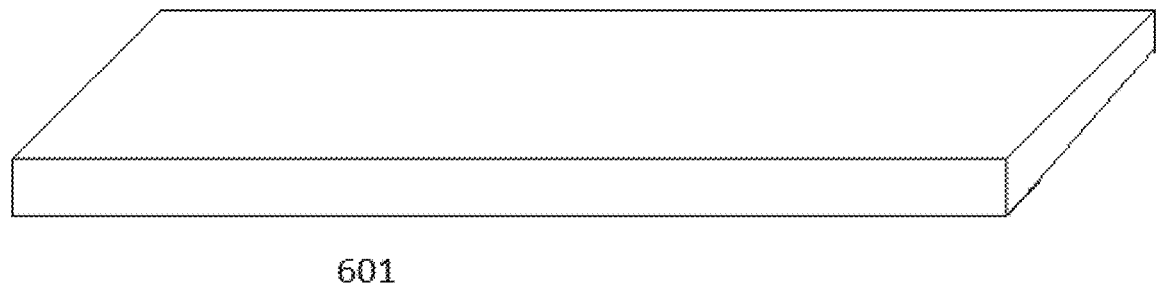
FIGS. 6A-D show examples of curvatures that can be used with a substantially planar sheet.
Figure 6B:
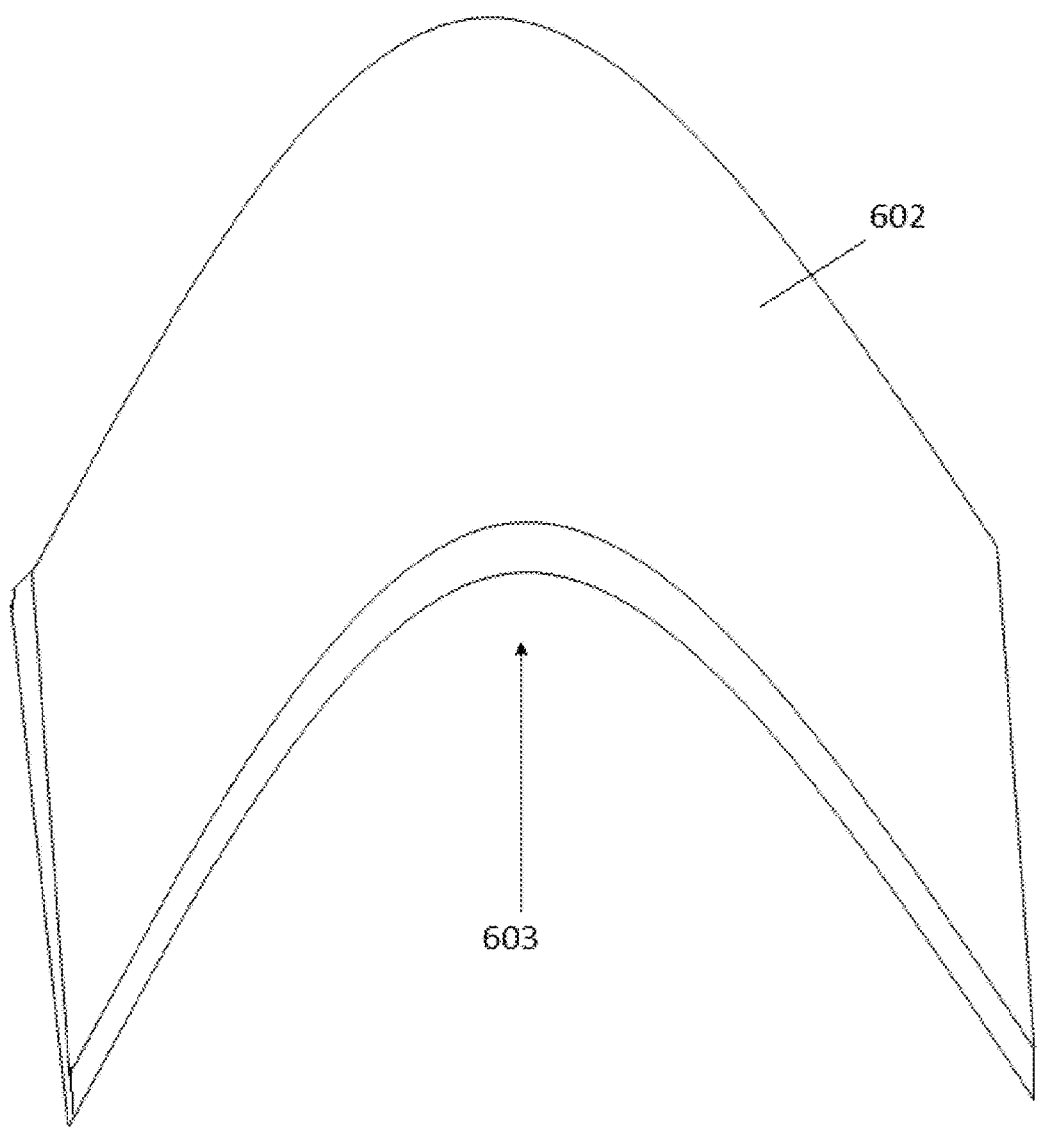
Figure 6C:
Figure 6D:
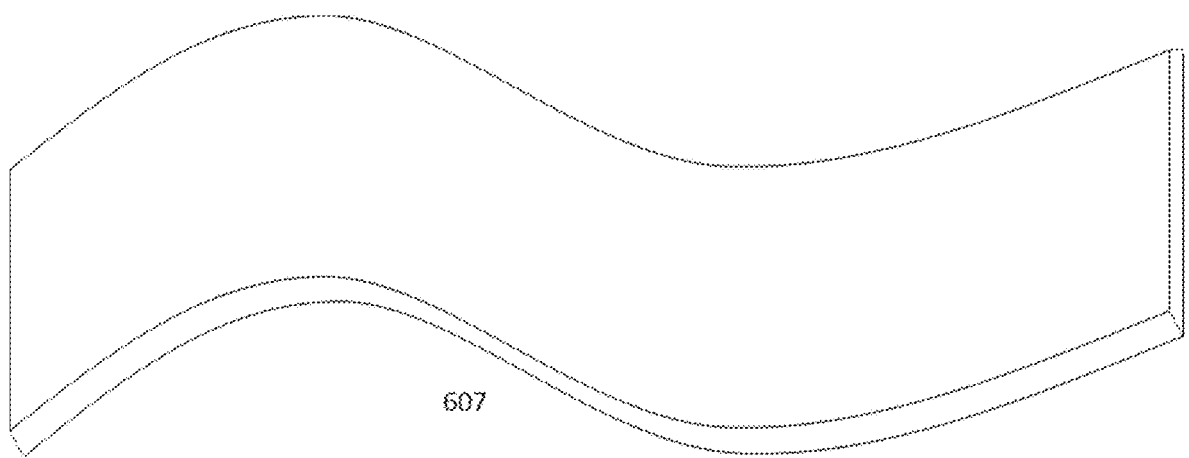

FIGS. 6A-6D show examples of types of curvatures that can be included in the substantially planar sheet. FIG. 6A shows a substantially planar sheet 601 that is substantially flat. FIG. 6B shows a substantially planar sheet 602 that has a curvature in a single dimension, shown by arrow 603. FIG. 6C shows a substantially planar sheet 604 that has curvatures in two dimensions. The substantially planar sheet 604 is curved as shown by arrow 605 as well as by arrow 606, forming a dome-like structure. FIG. 6D shows a substantially planar sheet 607 having an S-type curvature, which curves both directions through a first dimension. One of skill in the art will understand that the types of curvatures illustrated in FIGS. 6A-D are merely examples, and any type of curvature can be used with the substantially planar sheets.

Substantially planar sheets having a curvature in one or two directions can be desirable in certain embodiments. Most structures in the human body are not perfectly planar. To accommodate the shape of the body structures a mesh can be flexible enough to accommodate for the shape change or a structure that is deformable. A certain amount of planar strain is necessary to accommodate for a 2-dimensional curvature in the body, which can be better accomplished with a substantially planar sheet having a similar curvature.

In any embodiment, any of the layered materials used for the synthetic support structures can be fabricated using slot coating. The process refers to a deposition process whereby a substrate can be coated, or deposited, with a solution, liquid, slurry, or the like by flowing the solution, liquid, slurry, or the like, through a slot or mold of fixed dimensions that is placed adjacent to, in contact with, or onto the substrate onto which the deposition or coating occurs. Slot coating can be used to coat or deposit a liquid film onto a planar substrate for mating a flat mesh or patch. The film thickness can be controlled by a desired flow rate and speed.

The pore size of the substantially planar mesh can be between 0.2 and 5.0 mm to allow a bioink to interact with the substantially planar mesh. The pore size can be selected for proper density of the hydrogel encapsulated cells in the bioink based on necessary cell function, nutrient requirements, and oxygen feed. The substantially planar mesh can have a radial compliance between 1% and 20% $1/100$ mmHg, selected to roughly match the elasticity and stiffness of the target tissue or organ. One of skill in the art can select an elasticity based on the target tissue or organ.

In any embodiment, the substantially planar mesh can be manufactured by interlacing warp and weft yarn. Warp knitting can be used to create a desired geometric structure with controlled elasticity in any planar direction of the mesh. Weft knitting can be used to control thickness, provide consistent pore size and shape, and desired elongation and recovery properties.

In any embodiment, nonwoven structures produced by interlocking or bonding of fibers can also be used to create the substantially planar mesh. The nonwoven mesh structures can have a micro-porous structure. The nonwoven mesh structures can provide for fibrous tissue ingrowth and reduced adhesion. Although described as nonwoven, the substantially planar mesh can include the described nonwoven structure containing interlocking or bonding fibers.

Hernia Mesh

The described substantially planar meshes, patches, or constructs can be used to repair organs, hernias, or any tissue surface. The described substantially planar meshes, patches, or constructs can also be used to replace ruptured tissue. The described substantially planar meshes, patches, or constructs can promote cellular proliferation and tissue formation while concurrently creating a structure that provides mechanical stability for tissue development in vitro, during a maturation phase in a bioreactor. The engineered tissues can provide mechanical stability for tissue development during a degradation phase in vivo. In addition to surface repair, the described constructs can be used for replacement of esophagus and vagina tissues, tissue fabrication, cardiac patches, or any other suitable application known to those of skill in the art. The described engineered tissues can also be used for organoids for therapy development and testing to reduce animal testing.

In any embodiment, the tissue engineered patches and meshes can have one or more tissue stabilization anchors to secure the construct to surrounding tissue. The stabilization anchors can be a hook, loop, or latch. The stabilization anchors can also be sutures, pins, Velcro-like hooks, and the like. The stabilization anchor can form any part of the construct and be integrated into a supporting structure such as a fabric, braid, mesh, scaffold, and the like. In any embodiment, the described supporting structure can have one or more of the described stabilization anchors positioned in the mesh, scaffold, fabric, or braid portions to assist in integration with another material, such as a bioink or native tissue. The stabilization anchors can be positioned throughout the mesh, scaffold, fabric, or braid portions to provide adhesion points for an interpenetrating network between a first material and a second material. For example, the first material can be a bioink and the second material can be a braided polymer or suture material. In another example, the first material can be a braided polymer or suture material, and the second material native tissue.

In particular, the stabilization anchors can aid in the integration of any of the described tissue engineered constructs into host tissue after implantation or surgical placement. In certain embodiments, the material containing the stabilization hooks can degrade over time in vivo. The stabilization anchors can provide a mechanism to stabilize the engineered planar patch across an implant location as tissue ingrowth occurs. For example, hook knitting can be used to latch onto a planar area of tissue on an organ surface to encourage mechanical integration. In any embodiment, the scaffold can contain cells that are bio-printed or otherwise deposited into a void area of the scaffold.

Bioreactor/Maturing

The tissue engineered substantially planar sheets and patches can be matured in a bioreactor under pulsatile hydraulic and axial loading until desired properties are obtained. In any embodiment, a force can be loaded uniaxially or biaxially. The tissue engineered substantially planar sheets and patches can be seeded with cells at either a pre- or post-implantation stage. The cells can be endothelial cells and vascular smooth muscle cells and fibroblasts for the planar application, as well as their progenitor cells and associated stem cells. Any other cells known to possess anti-thrombogenic properties, minimize platelet aggregation, or clot formation can be used. The constructs can be non-immunogenic. The cells can also be remodeled under certain flow conditions and produce extracellular matrix proteins such as collagen and elastin.

In any embodiment, the substantially planar sheets and patches can be seeded using passive techniques. A cell suspension of cells can be pipetted directly onto substantially planar sheets or patches in any method known to one of ordinary skill. After application of the cell suspension to the substantially planar sheets and patches can be incubated with media to allow for cell attachment. In any embodiment, any surface of the substantially planar sheet or patch can be flushed with endothelial cells in the bioreactor. In other embodiments, cells can be seeded and adhered to a support structure with a biological glue. Fibrin or fibronectin can be used as the biological glue. Other adhesive coatings such as collagen, laminin, and plasma can also be used. Alternatively, ligands specific to particular cell types, such as, biomimetic surfactant polymers derived from one of the heparin-binding domains of fibronectin that promote adhesion and growth can be used. In other embodiments, cells can be adhered to a scaffold by using tropoelastin and fibrillins. The various coating methods can be implemented by dipping the scaffold into the glue or by applying pulsatile perfusion onto the scaffold with the biological glue.

In any embodiment, the tissue engineered vascular substantially planar sheets and patches can be seeded using dynamic techniques. Cell can be seeded by inducing hydrostatic forces, such as rotational or by creating pressure differentials, such as vacuum seeding. The techniques can increase cell seeding efficiency, uniformity, and/or penetration of the scaffold. For example, the described tissue constructs can be rotated about an axis in a cell/medium suspension or spun along with a cell/medium suspension at speeds and times known to those of skill in the art to produce a desired result and to spread material across a planar via centrifugal force. The described tissue construct can also be subject vacuum pressure to force a cell suspension through pores or void spaces of the scaffold.

During maturation, a cyclic force, such as axial tension, can be applied to the constructs. In one non-limiting embodiment, a cell growth medium can be flowed across substantially planar sheets and patches having autologous cells seeded thereon. The cell growth medium can include water, nutrients for the cells and cell signaling chemicals. The flow can replicate physiological conditions to induce remodeling of the cells. The cell growth medium can also be flowed across one or surfaces of the substantially planar sheets and patches to remodel the cells seeded thereon. One of skill in the art would be able to determine the proper hydraulic and axial loading during the maturation process based on the requirements for the final substantially planar sheets and patches.

One of skill can also determine suitable flow rates, timing, periods. After maturation, the tissue engineered substantially planar sheets can be implanted into a patient. One of skill in the art will understand that modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules.

What is claimed is:

1. A method for forming a tissue engineered substantially planar sheet, comprising the steps of:
    positioning a substantially planar mesh having a plurality of stabilization anchors, onto a substrate and filling a void space in the substantially planar mesh fully or partially with a bioink;
    placing the bioink on the substantially planar mesh by dip casting; and
    maturing the substantially planar sheet in a bioreactor.

2. The method of claim 1, wherein the stabilization anchor is a hook, loop, or latch.

3. The method of claim 1, where the substantially planar mesh is a weave, knit, braid, non-woven textile, or laser cut metal.

4. The method of claim 1, wherein the substantially planar mesh comprises one or more antibiotics or antibiotic agents.

5. The method of claim 4, wherein the antibiotic is minocycline and rifampin and the substantially planar sheet delivers the antibiotic into local tissue for at least 1 day after implantation.

6. The method of claim 4, wherein the substantially planar mesh is absorbed after implantation in about 9 weeks.

7. The method of claim 1, wherein the substantially planar mesh is a multi-filament knitted mesh.

8. The method of claim 1, wherein the substantially planar mesh has a pore size between 0.2 and 5.0 mm, and an elasticity matching a membrane stiffness of a target tissue or organ between 0.25 and 2.5 N/mm.

9. The method of claim 1, wherein the substantially planar mesh has a pore size between 0.2 and 5.0 mm, and an elasticity matching a membrane stiffness of a target tissue or organ between 0.675 and 1.265 N/mm.

10. The method of claim 1, wherein the substantially planar mesh has a pore size of at least 3 mm by 3 mm.

11. The method of claim 1, wherein the substantially planar mesh is biodegradable, bioabsorbable, or bioinert.

12. The method of claim 1, wherein the bioink is seeded with endothelial cells.

13. The method of claim 1, wherein one or more skeletal muscle cell layer, smooth muscle cell layer, myocardiocytes, pericytes, endothelial cells fibroblast layer, cord-blood derived cell layer, or combinations thereof is deposited on the bioink.

14. The method of claim 1, where the bioink comprises a hydrogel and cells.

15. A tissue engineered hernia patch produced by the method of claim 1, wherein the hernia patch has burst strength of at least 250 kPa, tensile strength of at least 100 N, and suture pull out strength of at least 25 N.

16. The tissue engineered hernia patch of claim 15, further comprising an anti-bacterial envelope.

17. The tissue engineered hernia patch of claim 16, wherein the anti-bacterial envelope contains the antimicrobial agents minocycline and rifampin.

18. A tissue engineered substantially planar sheet formed by steps comprising:
    positioning a substantially planar mesh having a plurality of stabilization anchors, onto a substrate and filling a void space in the substantially planar mesh fully or partially with a bioink;
    placing the bioink on the substantially planar mesh by dip casting; and
    maturing the substantially planar sheet in a bioreactor.

* * * * *